US00PP08785P

United States Patent [19]

VandenBerg

[11] Patent Number: Plant 8,785

[45] Date of Patent: Jun. 14, 1994

[54] CHRYSANTHEMUM PLANT NAMED GOLDEN GRACE

[75] Inventor: Cornelis P. VandenBerg, Salinas, Calif.

[73] Assignee: Yoder Brothers, Inc., Barberton, Ohio

[21] Appl. No.: 922,480

[22] Filed: Dec. 17, 1992

[51] Int. Cl.[5] ..... A01H 5/00

[52] U.S. Cl. ..... Plt./82.2

[58] Field of Search ..... Plt. 82.2, 82.3

[56] References Cited

U.S. PATENT DOCUMENTS 4,616,099 10/1986 Sparkes ..... 47/58

OTHER PUBLICATIONS

Broertjes, et al., 1980, "A mutant of a mutant of a . . . Irradiation of progressive radiation-induced mutants in a mutation-breeding programme with *C. morifolium*", Euphytica, 29:526–530.

Gosling, ed., 1979, "The Chrysanthemum Manual—6th edition", The National Chrysanthemum Society, London, Essex Telegraph Press, Ltd., pp. 329–326.

Broertjes, et al., 1978, "Application of Mutation Breeding Methods in the Improvement of Vegetatively Propagated Crops", Elsevier Sci. Pub. Co., New York, pp. 162–175.

Searle, et al., 1968, "Chrysanthemums the Year Round", Blanford Press, London, pp. 27–29, 320–327.

Chan, 1966, "Chrysanthemum and rose mutations induced by X-rays", Am. Soc. Hort. Sci. Proc., pp. 613–620.

Broertjes, 1966, "Mutation breeding of Chrysanthemums", Euphytica, 15:156–162.

Dowrick et al., 1966, "The induction of mutations in Chrysanthemums using X- and gamma radiation", Euphytica, 15:204–210.

*Primary Examiner*—Howard J. Locker

*Attorney, Agent, or Firm*—Foley & Lardner

[57] ABSTRACT

A Chrysanthemum plant named Golden Grace particularly characterized by its flat capitulum form; daisy capitulum type; golden yellow ray floret color; diameter across face of capitulum of 44 to 57 mm when fully opened; branching pattern is spreading and prolific, with 7 to 8 breaks after pinch when grown outside under natural daylength in fall flowerings, and 7 breaks after pinch when grown in 10 cm pots for spring flowerings; natural season flower date of September 1 when planting rooted cuttings on June 25 in Salinas, Calif., and September 30 to October 2 when planting rooted cuttings June 15 in Hightstown, N.J.; flowering response of 50 to 54 days after rooting in no light/no shade programs in spring; plant height of 33 cm when grown in fall under natural daylength with no growth regulators, and 18 cm when grown in 10 cm pots in spring with 1 application of 2500 ppm B-9 SP; and durable, uniform performance.

1 Drawing Sheet

The present invention comprises a new and distinct cultivar of Chrysanthemum, botanically known as *Dendranthema grandiflora,* and referred to by the cultivar name Golden Grace.

Golden Grace, identified as 83-628B01, is a product of a mutation induction program. The new cultivar was discovered and selected by Cornelis P. VandenBerg on Nov. 13, 1989, in a controlled environment in Salinas, Calif. as one flowering plant within a flowering block established as rooted cuttings from stock plants which had been exposed as unrooted cuttings to an X-ray source of 1750 rads in Fort Myers, Fla. on May 25, 1989. The irradiated parent cultivar was the cultivar identified as Grace, disclosed in U.S. Plant Pat. No. 7,642, and described as a flat daisy spray pot mum and garden mum with an orange-bronze ray floret color; diameter across face of capitulum of 44 57 mm when fully opened; spreading and prolific branching pattern, with 7 to 9 branches after pinch; average natural season flower date of August 26 to 31 in Salinas, Calif. and September 22 to 27 in Hightstown, N.J.; photoperiodic flowering response in no light/no shade programs in spring of 49 to 52 days; and durable, uniform performance. The above description of Grace has a wider range of values and measurements than disclosed in U.S. Plant Pat. No. 7,642 for Grace, based on continued flower trials after the application for Grace was filed.

The irradiation program resulting in Golden Grace had as its primary objective the expansion of color ranges of the parent cultivar Grace. The irradiation program comprised irradiating cuttings of the parent cultivar at irradiation levels of 1500, 1750 and 2000 rads. A total of 1435 cuttings harvested from a total of 225 irradiated plants were planted on Sep. 11, Sep. 4 and Aug. 21, 1989, respectively. Of these, 14 initial selections were made, which selections were then revegetated and reflowered. Four consecutive flowerings resulted in discarding 12 of the original 14 selections on Aug. 29, 1990. Two selections, identified as Dark Grace (8357) and Golden Grace (8391) were maintained as PIs (Possible Introductions) and trialed for one year, ultimately resulting in discarding Dark Grace on Sep. 23, 1991, and the decision to introduce Golden Grace.

The first act of asexual reproduction of Golden Grace was accomplished when vegetative cuttings were taken from the initial selection in December 1989 in a controlled environment in Salinas, Calif., by technicians working under supervision of Cornelis P. VandenBerg.

Horticultural examination of controlled flowerings of successive plantings has shown that the unique combination of characteristics as herein disclosed for Golden Grace are firmly fixed and are retained through successive generations of asexual reproduction.

Golden Grace has not been observed under all possible environmental conditions. The phenotype may vary significantly with variations in environment such as temperature, light intensity and daylength, without, however, any variance in genotype.

The following observations, measurements and comparisons describe plants grown in controlled open areas in Salinas, Calif., and in Hightstown, N.J. Rooted cuttings were established in soil and maintained outdoors under the natural temperature and daylength prevailing during June through October. Spring flowerings were conducted in Salinas, Calif. under greenhouse conditions which approximate those generally used in commercial practice for small pot spring garden mum production.

The following traits have been repeatedly observed and are determined to be basic characteristics of Golden Grace, which, in combination, distinguish this Chrysanthemum as a new and distinct cultivar.

1. Flat capitulum form.
2. Daisy capitulum type.
3. Golden yellow ray floret color.
4. Diameter across face of capitulum of 44 to 57 mm when fully opened.
5. Branching pattern is spreading and prolific, with 7 to 8 breaks after pinch when grown outside under natural daylength in fall flowerings, and 7 breaks after pinch when grown in 10 cm pots for spring flowerings.
6. Natural season flower date of September 1 when planting rooted cuttings on June 25 in Salinas, Calif., and September 30 to October 2 when planting rooted cuttings June 15 in Hightstown, N.J.
7. Flowering response of 50 to 54 days after rooting in no light/no shade programs in spring.
8. Plant height of 33 cm when grown in fall under natural daylength with no growth regulators, and 18 cm when grown in 10 cm pots in spring with 1 application of 2500 ppm B-9 SP.
9. Durable, uniform performance.

The accompanying photographic drawing is a color photograph of Golden Grace grown as a pinched pot mum and garden mum grown under controlled greenhouse conditions in Salinas, Calif., with the colors being as nearly true as possible with illustrations of this type.

Of the commercial cultivars known to the inventor, the most similar in comparison to Golden Grace is the parent cultivar Grace. Most traits of Golden Grace are similar to those of Grace, except for the ray floret color and the flowering response. The ray floret color of Golden Grace is golden yellow, while the ray floret color of Grace is orange-bronze. In most flowering trials, Golden Grace has been slower in flowering response by 2 to 8 days when compared with Grace.

In the following description color references are made to the Royal Horticultural Society Colour Chart. The color values were determined on plant material grown as a pinched pot mum and garden mum under controlled greenhouse conditions in Salinas, Calif. on Oct. 23, 1992.

Classification:

*Botanical.*—*Dendranthema grandiflora* cv Golden Grace.

*Commercial.*—Flat daisy spray pot mum and garden mum.

INFLORESCENCE

A. Capitulum:

*Form.*—Flat.

*Type.*—Daisy.

*Diameter across face.*—44 to 57 mm when fully opened.

B. Corolla of ray florets:

*Color (general tonality from a distance of three meters).*—Golden yellow.

*Color (upper surface).*—12A.

*Color (under surface).*—9A.

*Shape.*—Flat, straight, oblong. Older ray florets convex.

C. Corolla of disc florets:

*Color (mature).*—14B.

*Color (immature).*—Closest to 144B.

D. Reproductivity organs:

*Androecium.*—Present on disc florets only; moderate pollen.

*Gynoecium.*—Present on both ray and disc florets.

PLANT

A. General appearance:

*Height.*—33 cm when grown in fall under natural daylength with no growth regulators, and 18 cm when grown in 10 cm pots in spring with 1 application of 2500 ppm B-9 SP.

*Branching pattern.*—Spreading and prolific, with 7 to 8 breaks after pinch when grown outside under natural daylength in fall flowerings, and 7 breaks after pinch when grown in 10 cm pots for spring flowerings.

B. Foliage:

*Color (upper surface).*—147A.

*Color (under surface).*—147B.

*Shape.*—Moderately lobed.

I claim:

1. A new and distinct Chrysanthemum plant named Golden Grace, as described and illustrated.

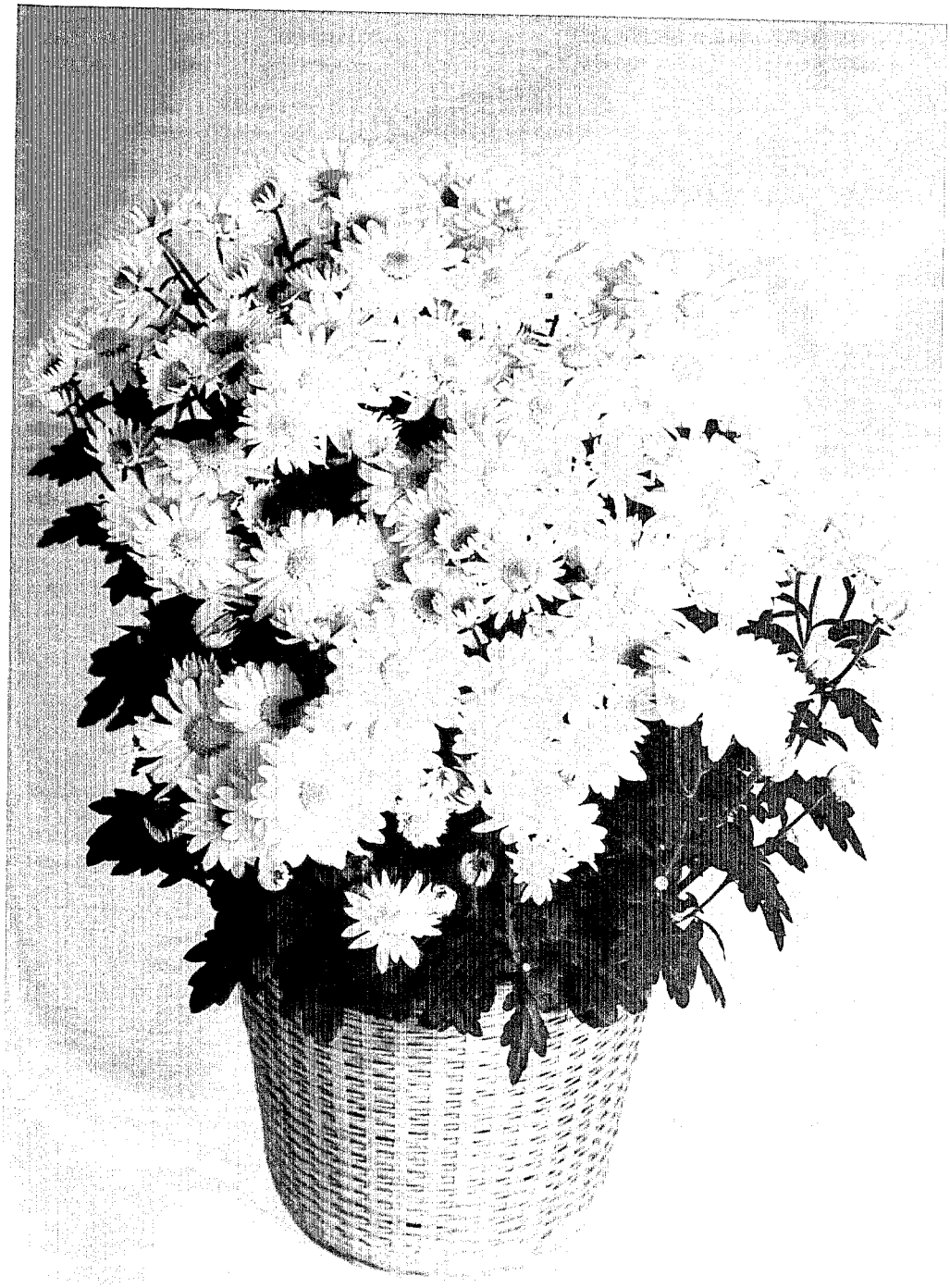

* * * * *